United States Patent [19]

Besenyei et al.

[11] Patent Number: 4,954,628
[45] Date of Patent: Sep. 4, 1990

[54] PROCESS FOR PREPARING N-SULPHONYL-UREAS

[75] Inventors: Gábor Besenyei; Sándor Németh; László Simándi; Mária Belák; Mária Szabó, all of Budapest; József Dukai, Veszprém; Lajos Nagy, Füzfőgyártelep; Elemér Tömördi, Veszprém; Csaba Söptei, Veszprém; Erzsébet E. Diószeginé, Veszprém, all of Hungary

[73] Assignees: Nitrokáelepek, Füfögyártelep; Magyar Tudományos Akadémia Kozponti Kémiai Kutató Intézete, Budapest, both of Hungary

[21] Appl. No.: 317,769

[22] Filed: Mar. 2, 1989

[30] Foreign Application Priority Data

Mar. 4, 1988 [HU] Hungary ............... 2251-1062/88

[51] Int. Cl.$^5$ ............... C07D 251/42; C07D 239/69; C07D 239/42; C07D 213/75
[52] U.S. Cl. ............................ 544/211; 544/212; 544/209; 544/207; 544/206; 544/198; 544/197; 544/300; 544/301; 544/310; 544/311; 544/316; 544/317; 546/284; 546/307; 546/308; 546/309; 546/291; 546/292; 546/293; 546/306; 564/39; 564/40; 564/42; 564/43; 544/319; 544/320; 544/321; 544/323; 544/324; 544/327; 544/331; 544/332; 544/322; 544/208; 558/61; 549/61; 549/62; 549/64; 549/65
[58] Field of Search ............... 544/197, 198, 208, 212, 544/310, 317, 321, 327, 322; 558/61; 564/39; 549/61; 546/284, 309, 293

[56] References Cited

U.S. PATENT DOCUMENTS 4,534,790 8/1985 Wolf ............................ 71/93

Primary Examiner—John M. Ford
Attorney, Agent, or Firm—Schweitzer & Cornman

[57] ABSTRACT

The invention relates to a process for preparing sulphonyl-ureas of the general formula (I)

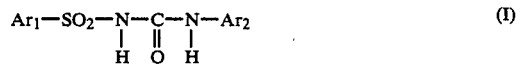

wherein $Ar_1$ represents a phenyl, naphthyl or thienyl group, the derivatives thereof substituted by $C_{1-4}$ alkyl, $C_{1-4}$ haloalkyl, (halo)alkoxycarbonyl, (halo)alkyloxy, nitro, cyano groups as well as by halogen atoms, $Ar_2$ represents a phenyl, pyridyl, pirimidinyl or triazinyl group and the derivatives thereof substituted by $C_{1-4}$ (halo)alkyl, $C_{1-4}$ (halo)alkyloxy, amino, O-acyl, O-arylsulphonyl, O-(substituted carbamoyl) groups as well as by halogen atoms.

According to the invention N-halogen aryl sulphonamidate is reacted in the presence of a carbonylating catalyst, carbon monoxide and an aromatic amine, optionally in the presence of a phase transfer catalyst, or N-halogen aryl sulphonamidate is reacted with carbon monoxide in the presence of a carbonylating catalyst, and optionally in the presence of a phase transfer catalyst, then the obtained reaction mixture is further reacted with an aromatic amine or an N-halogen-arylamine-alkali metal salt is reacted with aryl-sulphonamid in the presence of a carbonylating catalyst, carbon monoxide and optionally in the presence of a phase transfer catalyst or an amine, amine dihalogenid, aryl sulphonamid are reacted in the presence of a carbonylating catalyst and carbon monoxide and the obtained reaction mixture is worked up in a known manner.

The thus prepared sulphonyl-ureas are biologically active compounds, which are used in the pharmaceutical industry and for regulating plant growth.

16 Claims, No Drawings

PROCESS FOR PREPARING N-SULPHONYL-UREAS

The invention relates to a process for preparing N-sulphonyl ureas of the general formula (I)

$$Ar_1-SO_2-\underset{H}{N}-\underset{O}{\overset{\|}{C}}-\underset{H}{N}-Ar_2 \qquad (I)$$

Among the N-sulphonyl urea derivatives there are numerous biologically active compounds, a great number thereof have herbicidal, plant growth regulating and pharmaceutical effect.

The following processes are known for preparing the above compounds:

In EP-PS 01514, US-PS 4,190,432 and DE-PS 2,715,786 aryl-sulphonyl-isocyanates and amino triazines or aminopyrimidines are reacted for the synthesis of aryl sulphonyl ureas. The reaction is carried out in inert solvent (such as $CH_2Cl_2$, THF, acetonitrile), generally at room temperature under intensive stirring. The reaction can be characterized by the following equation (1):

$$Ar_1SO_2NCO + Ar_2NH_2 \rightarrow Ar_1SO_2NHC(O)NHAr_2 \qquad (1)$$

Aryl sulphonyl ureas are obtained also in case if a heterocyclic compound containing nitrogen substituted by an isocyanate group is reacted with N-arylsulphonamides. This method is suggested among others in EP-PS 51,465, EP-PS 30,140 and EP-PS 44,808. The reaction is shown in the following equation (2):

$$Ar_1SO_2NH_2 + Ar_2NCO \rightarrow Ar_1SO_2NHC(O)NHAr_2 \qquad (2)$$

Aryl sulphonyl ureas can also be prepared by reacting N-sulphonyl urea acid esters with amino triazines or amino pyrimidine or reacting N-triazinyl- or (pyrimidinyl)-urea acid esters with sulphonamides. This method is widely used according to EP-PS 44,809, EP-PS 178,101,, US-PS 4,662,933. The reaction generally takes place in the presence of a strong base (1,4-diazabicyclo[2.2.2]-octane /DABCO/, 1,8-diazabicyclo[5.4.0]undecene-7-/DBU/, Me₃Al) according to equations (3, 4) as follows:

$$Ar_1SO_2NHC(O)OR + Ar_2NH_2 \rightarrow Ar_1SO_2NH\text{-}C(O)NHAr_2 + ROH \qquad (3)$$

$$Ar_1SO_2NH_2 + R'O(O)CNHAr_2 \rightarrow Ar_1SO_2NH\text{-}C(O)NHAr_2 + R'OH \qquad (4)$$

The reaction of N-methyl-sulphonyl-carbamoylchlorides and aminotriazines or amino-pyrimidines also results in the formation of sulphonyl ureas. This kind of reaction is described among others in EP-PS 01,514, EP-PS 30,138, EP-PS 13,480 according to the following equation (5):

$$Ar_1SO_2N(Me)C(O)Cl + Ar_2NH_2 \rightarrow Ar_1SO_2N(Me)C(O)NHAr_2 + HCl \qquad (5)$$

Common characteristic of the known methods is that the preparation of one of the starting components is based on the direct or indirect use of phosgene. As it is well known phosgene is strongly toxic, its handling, delivery and storage requires special attention and its use means a constant source of danger. A further disadvantage is that the preparation of the widely used arylsulphonyl isocyanates with phosgene can be carried out at relative high temperature (110°–160° C.), the reactions are therefore very energy consuming. Further disadvantage of the above methods is that the isocyanates and carbamates of equations (1)–(4) can only be obtained often by a multistep synthesis, and a very fine hasardous catalyst (Me₃Al) should be used in some of the coupling reactions.

During our searches for preparing N-sulphonyl ureas by new processes it was found that the end product of the general formula (I) can also be obtained by reacting an N-halogen-aryl-sulphonamidate, aromatic amine and carbonmonoxide or N-halogen aromatic amine, sulphonamide and carbon monoxide in the presence of a catalyst, or after carbonylation (treating with carbon monoxide) reacting the N-halogen-sulphonamidate with aromatic amine.

The process according to the invention for preparing sulphonyl ureas of the general formula (I) wherein Ar₁ represents a phenyl, naphthyl or thienyl group, and the derivatives thereof substituted by $C_{1-4}$ alkyl, $C_{1-4}$ haloalkyl, (halo)-alkoxycarbonyl, (halo)alkyloxy, nitro, cyano group, as well as halogen atoms, Ar₂ represents a phenyl, pyridyl, pyrimidinyl or triazinyl group, and the derivatives thereof substituted by $C_{1-4}$ (halo)alkyl, $C_{1-4}$ (halo)alkyloxy, amino, O-acyl, O-aryl-sulphonyl, O-(substituted carbamoyl)-groups as well as halogen atoms, can be characterized in that (a) N-halogen-arylsulphonamidate of the general formula (II)

$$Ar_1-SO_2-\underset{Y}{\overset{|}{N}}-X \qquad (II)$$

wherein

Ar₁ is as defined above,

X stands for chloro or bromo atom,

Y stands for natrium ion, potassium ion, quaternary ammonium or quaternary phosphonium ion, is reacted according to reaction scheme (A) in the presence of a carbonylating catalyst, carbon monoxide and an aromatic amine of the general formula (III)

$$Ar_2-NH_2 \qquad (III)$$

wherein Ar₂ is as defined above—optionally in the presence of a phase transfer catalyst, or (b) N-halogenaryl-sulphonamidate of the general formula (II) is reacted with carbon monoxide according to reaction scheme (B) in the presence of a carbonylating catalyst, and optionally in the presence of a phase transfer catalyst, then the obtained reaction mixture is reacted with aromatic amine of the general formula (III), or (c) an N-halogenarylamine of the general formula (IV)

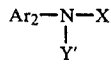 (IV)

wherein
Ar$_2$ and X are as defined above,
Y' stands for hydrogen atom, sodium or potassium ion
is reacted according to reaction scheme (C) in the presence of carbon monoxide and aryl sulphonamide of the general formula (V)

$$Ar_1-SO_2-NH_2 \quad (V)$$

wherein
Ar$_1$ is as defined above—and optionally in the presence of a phase transfer catalyst, or (d) an amine of the general formula (III), amine-N,N-dihalogenide of the general formula (VI)

$$Ar_2-NX_2 \quad (VI)$$

and aryl-sulphonamide of the general formula (V) are reacted according to reaction scheme (D) in the presence of a carbonylating catalyst and carbon monoxide.

As carbonylating catalyst a previously prepared or in the reaction mixture in situ prepared palladium containing complex is used, wherein the coordinative bond is made by carbon, nitrogen, oxygen, phosphorus, sulphur and/or halogen atoms, in the form of homogeneous, heterogeneous or immobilized homogeneous catalyst, in an amount of $10^{-2}$–10 weight% related to the weight of the starting N-halogen compounds. Phase transfer catalyst can also be used in an amount of $10^{-1}$–10 weight% calculated to the weight of the starting N-halogen compound. The reaction medium is an organic solvent, its temperature is between $-20°$ and $130°$ C., starting Co partial pressure is 0.3–10 MPa, reaction time: 0.5–24 hours. The reaction mixture is worked up in a known manner.

Process variants (a), (b), (c) and (d) can be shown in the following reaction schemes (A), (B), (C) and (D):

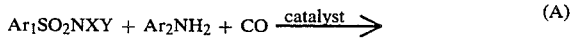 (A)

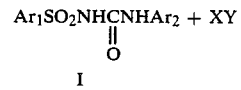
I

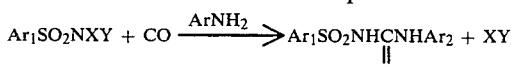 (B)

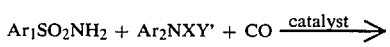 (C)

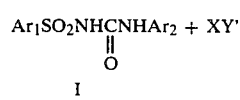
I

 (D)

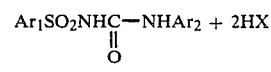
I

An advantageous starting compound is sulphonamidate of the general formula (II), wherein X is chlorine atom, Y is potassium ion.

A preferred starting compound is furthermore sulphonamidate of the general formula (II), wherein X is chlorine atom and Y is quaternary ammonium ion.

According to an advantageous process variant of the invention sodium or potassium salt of (N-chloroamino)-triazine is carbonylated in the presence of aryl-sulphonamide. According to a similarly preferred embodiment potassium-N-2-dichlorophenyl sulphonamidate is carbonylated in the presence of 2-amino-4-methyl-6-methoxy-triazine or 2-(N-chloro-amino)-4-methyl-6-methoxy-triazine-sodium salt in the presence of 2-methoxy-carbonyl-benzenesulphonamide.

As phase transfer catalyst quaternary ammonium salt, quaternary phosphonium salt or compounds of crown ether type are used.

The carbonylation is carried out optionally at a temperature between $20°$–$100°$ C.

The palladium catalyst can be used together with the carbonyls of metals belonging to group VI of the periodical system and/or with the complexes of metals belonging to group VIII of the periodical system.

An essential difference against the known processes described by equations (1)–(5) is that
arylsulphonyl-urea is prepared without using phosgene; and
the end product can be prepared from the starting compounds in a single step.

Important advantages of the process according to the invention can be summarized as follows:
use of phosgene is not necessary, so the process is more secure and does not endanger the environment as the known ones;
N-halogen-compounds used as starting compounds can be prepared with good yield from suitable starting materials by using cheap reagents (such as NaOCl, Ca(OCl)Cl, Cl$_2$, Br$_2$ etc.).
Both the carbonylating and the coupling reaction can be carried out at room temperature so energy can be saved.
N-halogen-sulphonamidates used as starting materials are known compounds in the art, their preparation methods are described in several literature references (see Methoden der Organischen Chemie /Houben-Weyl/, Band IX, page 642, 1955; M. C. Campbell and G. Johnson: Chem. Rev., 1978, 78/1/, 65–79. Bull. Chem. Soc. Jpn. 1984, 57, 3341-2).

It is generally preferred to use N-halogen-sulphonamidate in previously prepared and purified form in order to avoid undesired side-reactions (e.g. poisoning of the catalyst).

Only few references can be found in the literature concerning amine-monohalogenides and amine-dihalogenides of the general formulae (IV) and (VI) (of DE-PS 2,018,719 and J. Chem. Soc. Perkins I. 1977 1746).

According to the process of the invention the sulphonyl-urea synthesis is carried out in a solvent. As reaction medium any solvent generally used in the art such as petrolether, hexane, octane, cyclohexane, benzene and its homologues, dichloromethan, chloroform, carbon-tetrachloride, mono- and polychlorinated derivatives of $C_2$–$C_6$ saturated and $C=C$ bond containing hydrocarbons, simple aliphatic and cycloaliphatic ketones (e.g. acetone, methyl-ethyl-ketone, cyclohexanone), simple aliphatic esters (ethyl-formate, ethyl-acetate, butyl-acetate), esters of carbon dioxide (dimethyl-carbonate, diethyl-carbonate, ethylene-carbonate, propylene-carbonate), acid amides (DMF, dimethyl-acetamide, hexamethyl-phosphorus acid triamide), nitriles (acetonitrile, benzonitrile), ethers (diethyl ether, diisopropyl ether) can be used.

In order to accelerate the carbonylation reaction of the N-monochloro compound a catalyst is used. As catalyst any transitional metal, the oxides, salts, carbonyls and complexes thereof, formed with ligandums containing nitrogen, phosphorus, sulphur, oxygen atom, as well as the mixtures thereof can be used. The catalyst can be used in homogeneous, heterogeneous and heterogenated (immobilised) homogeneous form, it can be added in a previously prepared form, or can be generated in situ in the reaction mixture. As carrier of the heterogenous and immobilized catalyst aluminium oxide, silica gel, active carbon and organic polymer type carrier can be used.

The catalyst can be added in a ratio of $10^{-2}$–10 weight% related to the amount of the starting monochloro compound.

The recovery method of the catalyst depends on the type of the catalyst used. In the reaction mixture on room temperature weakly soluble catalysts and catalyst with a carrier can be removed by simple filtration. Dissolved catalyst can be recovered from the reaction mixture during its working up by precipitation, separation, extraction, adsorption and other methods which are selected taking the chemical and physical characteristics of the catalyst into consideration.

The carbon monoxide used to the carbonylation can be used in pure form or as a gas mixture, e.g. by mixing it with air. Some catalysts or reactants may, however, be sensitive for some carbon monoxide diluting components, therefore the amount and quality of the diluting components allowable in case of the individual catalysts and reactants can be different. The partial CO-pressure of the reactor is preferably choosen between $10^4$ and $10^7$ Pa.

The carbonylation is carried out at a temperature between $-20°$ and $130°$ C., preferably at $20°$–$100°$ C. The proper temperature is depending on the activity of the catalyst or the thermic stability of the reaction components, resp.

N-halogen derivatives of sulphonamides are generally weakly soluble in organic solvents. In order to achieve an appropriate reaction speed the use of phase transfer catalyst can be necessary. For this purpose quaternary ammonium salts, quaternary phosphonium salts or crown ether type compounds may be used.

As crown ether type compound
dicyclohexyl-18-crown-6,
18-crown-6, (1,4,7,10,13,15-hexaoxacycloocta-decane and
dibenzo-18-crown-6
can be mentioned.

According to a process variant of the invention N-halogen-arylsulphonamidate of the general formula (II) is reacted with aromatic amines in the presence of carbonylation catalyst, carbon monoxide and optionally of phase transfer catalyst, or the N-halogen-sulphonamidate of the general formula (II) is subjected to catalytic carbonylation and the thus-prepared intermediate is reacted with aromatic amine. According to an other process variant haloamine of the general formula (IV) is reacted with sulphonamide of the general formula (V) in the presence of a catalyst, carbon monoxide and optionally of a phase transfer catalyst.

According to a preferred embodiment of the process of the invention an amino group containing component is also present in the reaction mixture during the carbonylation. The two-step reaction is taken place in this case parallelly.

The amino group-containing component can also be added to the reaction mixture after the carbonylation. The coupling reaction can in this case be carried out in the same solvent as the carbonylation. It is also possible to remove the solvent by mild heat treatment (perhaps in vacuo) and to carry out the reaction in a new solvent. In addition to the possibility of changing the solvent, the two-step solution promotes the better utilization of the pressure tight apparatuses.

According to the process of the invention the presence of a catalyst or additive to the coupling reaction of the components with $NH_2$ group content is generally not necessary.

After the coupling reaction the product is removed by filtration or in case of a not easily filterably liquid or well soluble product by precipitation or the end product is isolated by removing the solvent under mild circumstances. The thus-prepared sulphonyl ureas can be purified by using known methods.

The process according to the invention is described in detail in the following Examples. The obtained product is identified in all Examples by mass spectrometry (fast atom bombardment technique) and the quantity analysis was carried out by HPLC (high performance liquid chromatography).

EXAMPLE 1

2.28 g. (0.01 mole) of N-chloro-p-toluenesulphonic acid Na salt, 0.14 g. $PdCl_2$, 0.2 $cm^3$ of acetonitrile and 10 $cm^3$ of dichloromethane were placed into a pressure tight autoclave and after rinsing the gas phase with CO several times the pressure of carbon monoxide was adjusted to MPa 5.0. The carbonylation was continued for 5 hours at room temperature under stirring. After the calculated amount of CO had become exhausted the gas phase was blown off and the reaction mixture was transferred into a glass equipment. 1.4 g. (0.01 mole) of 2-amino-4-methyl-6-methoxy-triazine were given to the reaction mixture and was stirred for 16 hours hermetically sealed. The solvent was removed in vacuo, the solid part was dissolved in the mixture of 100 ml. of water and 0.3 g. of $K_2CO_3$/0.5 g. of solid product. The insoluble part was removed by filtration and the product was removed from the filtrate by acidifying the solution until pH=3. The product can be further purified by crystallization if necessary. Yield: 2.45 g. of N-p-toluene-sulphonyl-N'-(4-methyl-6-methoxy-2-triazinyl)urea (72.5%).

EXAMPLE 2

The process according to Example 1 was followed with the difference that 2.0 g. (9.4 mmoles) of N-chlorobenzenesulphonic acid amide Na salt was used as starting compound, which was coupled with 1.31 g. (9.4 mmoles) of 2-amino-4-methyl-6-methoxy-triazine after the carbonylation reaction. Yield: 2.15 g. (70.8%) of N-benzenesulphonyl-N'-(4-methyl-6-methoxy-2-triazinyl)-urea.

EXAMPLE 3

The process according to Example 1 was followed with the difference that as coupling agent 1.27 g. (0.01 mole) of 2-chloroaniline was used. Yield: 2.1 g. (64.8%) of N-p-toluensulphonyl-N'-(2-chlorophenyl)-urea. Mp.: 164°–166° C.

Characteristic IR spectra: 3305.9; 3059.5; 1697.1; 1351.8 and 1123.4 cm$^{-1}$.

EXAMPLE 4

2.28 g. (10 mmoles) of 4-MePhSO$_2$NClNa, 46.7 mg. of palladium chloride, 10.0 cm$^3$ of dichloromethane and 0.5 cm$^3$ of acetonitrile were filled into a pressure tight reactor and after rinsing the reactor with carbon monoxide the CO pressure was adjusted to MPa 4.1. The reaction mixture was stirred for 6 hours at room temperature then after blowing off the gas phase by using outer cooling 1.28 g. (10 mmoles) of 2-chloroaniline were added under N$_2$ atmosphere dropwise. After stirring for further 10 minutes the white precipitate containing reaction mixture was evaporated to dryness. The weight of the isolated precipitate was 3.56 g. and N-(4-Me-phenyl-sulphonyl)-N'-(2-chlorophenyl)-urea was obtained according to the HPLC analysis with a yield of 78%. The following compounds /N-(Ar$_1$-sulphonyl)-N'-Ar$_2$-urea/ were prepared according to the parameters disclosed in Table 1 at different temperatures using the process described in Example 4. (When preparing amino-triazine derivatives after the addition of the amino-triazine component the reaction mixture was stirred for 14 hours.

TABLE 1

| Number of Example | Ar$_1$ | Ar$_2$ | Catalyst | Complex forming agent | Solvent | Temp. (°C.) | Time (hour) | Yield (%) |
|---|---|---|---|---|---|---|---|---|
| 5 | 4-Me-phenyl** | 2-Chlorophenyl | PdCl$_2$ 46,8 mg | CH$_3$CN 0,5 cm$^3$ | CH$_2$Cl$_2$ 10 cm$^3$ | 45 | 2,5 | 76 |
| 6 | 4-Me-phenyl | 2-Chlorophenyl | PdCl$_2$ 50,0 mg | CH$_3$CN 0,5 cm$^3$ | CH$_2$Cl$_2$ 10 cm$^3$ | 65 | 1,25 | 80 |
| 7 | 4-Me-phenyl | 2-Methylphenyl | PdCl$_2$ 51,1 mg | CH$_3$CN 0,5 cm$^3$ | CH$_2$Cl$_2$ 10 cm$^3$ | 85 | 0,5 | 81 |
| 8 | 4-Me-phenyl | 2-Chlorophenyl | PdCl$_2$ 48,2 mg | CH$_3$CN 0,5 cm$^3$ | CH$_2$Cl$_2$ 10 cm$^3$ | 105 | 0,3 | 81 |
| 9 | 2-Cl-phenyl* | 2-Methyl-6-methoxy-triazin-2-yl | PdCl$_2$ 30 mg | — | CH$_3$CN 10 cm$^3$ | 0 25 | 3,5 1,5 | 74 |

*Potassium salt
**Methyl

EXAMPLE 10

The process described in Example 4 is followed for preparing N-(4-Me-phenyl-sulphonyl)-N'-(2-chlorophenyl)-urea with the difference that the starting CO pressure was varied according to Table 2. The reaction parameters and the obtained yield are summarized in Table 2.

TABLE 2

| Number of Example | Temperature (°C.) | P$_{CO}$ (MPa) | Time (hour) | Catalyst | Additive | Yield (%) |
|---|---|---|---|---|---|---|
| 10 | 60 | 0.8 | 4.0 | PdCl$_2$ 80 mg | PhCN 2 cm$^3$ | 76 |
| 11 | 25 | 1.5 | 9.5 | PdCl$_2$ 52.1 mg | CH$_3$CN 0.5 cm$^3$ | 86 |
| 12 | 25 | 6.0 | 5.0 | PdCl$_2$ 110 mg | CH$_3$CN 0.5 cm$^3$ | 81 |
| 13 | 25 | 9.0 | 3.8 | PdCl$_2$ 50 mg | CH$_3$CN 0.5 cm$^3$ | 68 |

EXAMPLE 14

The process described in Example 1 was followed with the difference that the sulphonamidate compounds were used together with different cationes or phase transfer catalysts which were added during the reaction. The yield of the thus-obtained Ar$_2$SO$_2$NHCONHAr$_2$ compounds of the general formula (I) and the reaction parameters are detailed in Table 3.

TABLE 3

| Number of Example | Ar$_1$SO$_2$NXY | Ar$_2$NH$_2$ | Catalyst | Additive | Temperature (°C.) | Time (hour) | Yield (%) |
|---|---|---|---|---|---|---|---|
| 14 | PhSO$_2$NClNa | 2-Amino-4-methyl-6-methoxy-triazine | PdCl$_2$ 145 mg | CH$_3$CN 0,2 cm$^3$ | 25 | 6 | 70,8 |
| 15 | 4-MePhSO$_2$NClK | 2-Cl-aniline | Pd$_2$dba$_3$ 168 mg | — | 25 50 | 1,2 1,3 | 85 |
| 16 | 2-ClPhSO$_2$NClK | 2-Amino-4-methyl-pyrimidine | Pd(PhCN)$_2$Cl$_2$ 96 mg | PhCN 0,5 cm$^3$ | 50 | 1,5 | 88 |
| 17 | 2-BrPhSO$_2$NClK | 2-Amino-4,6-dimethyl-pyrimidine | PdCl$_2$ 67 mg | CH$_3$CN 0,3 cm$^3$ | 80 | 1,1 | 85 |
| 18 | 4-MePhSO$_2$NCl$^-$ Bu$_4$N$^+$ | 2-Cl-aniline | PdCl$_2$ 27 mg | CH$_3$CN 0,2 cm$^3$ | 25 | 2,5 | 71 |
| 19 | 2-ClPhSO$_2$NClK | 2-Cl-aniline | Pd(Ph$_3$P)$_2$Cl$_2$ 70,4 mg | CH$_3$CN 1,0 cm$^3$ Et$_3$(PhCH$_2$)N$^+$Cl$^-$ | 25 | 3,5 | 78 |

TABLE 3-continued

| Number of Example | Ar₁SO₂NXY | Ar₂NH₂ | Catalyst | Additive | Temperature (°C.) | Time (hour) | Yield (%) |
|---|---|---|---|---|---|---|---|
| 20 | 2-ClPhSO₂NClK | 2-Cl-aniline | PdCl₂ 85 mg | 112 mg CH₃CN 1 cm² Bu₄P⁺Cl⁻ 47 mg | 35 | 3,5 | 81 |
| 21 | 4-MePhSO₂NClK | 2-Cl-aniline | Pd(Ph₃P)₂Cl₂ 150 mg | Dicyclo-hexyl-18-crown-6 32 mg | 25 | 3,0 | 78 |

EXAMPLE 22

3.05 g. (10 mmoles) of potassium-2-bromo-phenylsulphonamidate, 1.4 g. of 2-amino-4-methyl-6-methoxytriazine, 2.0 cm³ of benzonitrile were filled into a pressure tight reactor having a volume of 45 cm³ and after rinsing it several times the pressure of carbon monoxide was adjusted to MPa 4.0. The reactor was heated to 60° C. under stirring and thermostated at this temperature for 1½ hours. After cooling the reaction mixture was concentrated, the separation of the precipitate was completed with ether, the precipitate was filtered, washed and dried. According to the HPLC method 77% of the organic substance-content of the isolated material was N-(2-bromophenyl-sulphonyl)-N'-(4-methyl-6-methoxytriazinyl)-urea. Further compounds of the general formula (I) were prepared similarly according to the data shown in Table 4.

dichloroamino)-4-methyl-6-methoxytriazine, 139 mg. of PdCl₂, 10 cm³ of dichloromethane as well as 0.3 cm³ of acetonitrile were filled into a pressure tight reactor and the pressure of carbon monoxide was adjusted to MPa 3.5. After stirring at room temperature for 5.5 hours N-(2-methoxycarbonyl)-phenyl-sulphony)-N'-(4-methyl-6-methoxytriazinyl)-urea was obtained with a yield of 3%.

EXAMPLE 31

The process according to Example 4 was followed for preparing compounds of the general formula (I) with the difference that the additive/catalyst ratio, the substrate/catalyst ratio as well as the quality of the catalyst were changed. The starting pressure of CO was MPa 4.0-6.0 and if other solvent is not mentioned the solvent was CH₂Cl₂, Ar₂=2-Cl-phenyl group, the amount of the substrate was 10 mmoles of N-chlorosulphonamidate sodium or potassium salt. The data are summarized in Table 5.

TABLE 4

| Number of Example | Ar₁SO₂NXY, and Ar₁SO₂NH₂, resp. | Ar₂NH₂, and Ar₂NX₂, resp. | Catalyst | Additive | Temp. (°C.) | Time (hour) | Yield (%) |
|---|---|---|---|---|---|---|---|
| 23 | 4-MePhSO₂NClNa | 2-Amino-4-methyl-6-methoxy-triazine | PdCl₂ 99 mg | CH₃CN 0,2 cm³ | 25 | 15 | 75 |
| 24 | 2-ClPhSO₂NClK | 2-Amino-4-methyl-6-methoxy-triazine | PdCl₂ 125 mg | CH₃CN 0,2 cm³ | 25 | 9 | 70 |
| 25 | 2-MeOC(O)PhSO₂NH₂ 2,15 g | 2-(N-Chlor-amino)-4-methyl-6-methoxy-triazine Na-salt 1,46 g | PdCl₂ 112 mg | CH₃CN 1,0 cm³ | 25 | 6,3 | 30 |
| 26 | 2-MeOC(O)PhSO₂NH₂ 2,15 g | 2-(N-Chlor-amino)-4-methyl-6-methoxy-triazine K-salt 1,8 g | Pd(Ph₃P)₂Cl₂ 97 mg | — | 25 | 2 | 40* |
| 27 | 4-MePhSO₂NClK 2,40 g | 2-Amino-4-methyl-6-methoxy-triazine 1,40 mg | Pd(Ph₃P)₂Cl₂ 87 mg | Benzyl-triphenyl-phosphonium-chlorid | 65 | 1,5 | 77 |
| 28 | 4-MePhSO₂NClK 2,40 g | 2-Amino-4-methoxy-6-methoxy-methyl-triazine 1,70 g | Pd(Ph₃P)₂Cl₂ 127 mg | — | 65 | 1 | 75 |
| 29 | 2-ClPhSO₂NH₂ 1,91 g | 2-(N-Chlor-amino)-4-methyl-6-methoxy-triazine Na-salt 2,0 g | Pd(Ph₃P)₂Cl₂ 97 mg | — | 65 | 3,5 | 60 |
| 29A | 2-methoxy-carbonyl-3-amino-sulphonyl-thiophene 2,2 g | 2-(N-chloro-amino)-4-methyl-6-methoxy-triazine K-salt 2,5 g | Pd(PhCN)₂Cl₂ 160 mg | PhCN 0,5 cm³ | 40 | 3,0 | 51 |

*related to the potassium salt

EXAMPLE 30

2.15 g. of 2-MeOC(O)PhSO₂NH₂, 0.7 g. of 2-amino-4-methyl-6-methoxytriazine, 1.05 g. of 2-(N,N-

TABLE 5

| Number of Example | Ar₁ | Catalyst | Additive | Temperature (°C.) | Time (hour) | Yield (%) |
|---|---|---|---|---|---|---|
| 31 | 4-Me-phenyl | PdCl₂ 150 mg | CH₃CN 0,2 cm³ | 25 | 6 | 75 |

TABLE 5-continued

| Number of Example | Ar₁ | Catalyst | Additive | Temperature (°C.) | Time (hour) | Yield (%) |
|---|---|---|---|---|---|---|
| 32 | 2-Cl-phenyl | PdCl₂ 27 mg | PhCN 2,0 cm³ | 25 | 24 | 65 |
| 33 | 4-Me-phenyl | PdCl₂ 8,6 mg | CH₃CN 0,5 cm³ | 70 | 3,5 | 65 |
| 34 | 2-Cl-phenyl | PdCl₂ 30 mg | CH₃CNᵃ 10 cm³ | 0 / 25 | 3,5 / 1,5 | 74 |
| 35 | 4-Me-phenyl | PdCl₂ 55 mg | PhCN 0,2 cm³ | 25 | 18,5 | 79 |
| 36 | 4-Me-phenyl | PdCl₂ 104 mg | PhCNᵃ 10 cm³ | 25 | 1,3 | 75 |
| 37 | 4-Me-phenyl | Pd(py)₂Cl₂* 150 mg | PhCN | 80 | 1,5 | 68 |
| 38 | 4-Me-phenyl | Pd₂dba₃ 103 mg | CH₃CN 0,5 cm³ | 25 | 2 | 72 |
| 39 | 4-Me-phenyl | Pd₂dba₃ 168 mg | — | 80 | 1 | 85 |
| 40 | 2-Br-phenyl | Pd(Ph₃P)₂Cl₂ 198 mg | PhCN 2,0 cm³ | 60 | 0,25 | 80 |
| 41 | 4-Me-phenyl | Pd₂Cl₂dppm*** 54,5 mg | CH₃CN 0,5 cm³ | 25 | 12,5 | 68 |
| 42 | 4-Me-phenyl | Pd(OAc)₂ 120 mg | PhCN 2,0 cm³ | 80 | 2 | 72 |
| 43 | 4-Me-phenyl | /Pd(CO)Cl/ₙ 110 mg | — | 80 | 1 | 75 |
| 44 | 2-Br-phenyl | Pt(Ph₃P)₄ 21,5 mg Pd(Ph₃P)₂Cl₂ 66 mg | PhCN 0,5 cm³ | 65 | 2 | 81 |
| 45 | 2-Br-phenyl | Rh(Ph₃P)₃Cl 30 mg Pd(Ph₃P)₂Cl₂ 73 mg | PhCN 0,5 cm³ | 65 | 2 | 74 |
| 46 | 4-Me-phenyl | Pd(Ph₃P)₂Cl₂ 3 mg | — | 75 | 24 | 53 |
| 47 | 4-Me-phenyl | Mo(CO)₆ 100 mg Pd(Ph₃P)₂Cl₂ 100 mg | — | 55 | 0,75 | 83 |

— = without solvent
*py = Pyridine
**dba = Dibenzilyden-aceton;
***dppm = bis (Diphenylphosphino)-methane

EXAMPLE 48

The process described in Example 4 was followed with the difference that the substitutes of Ar₁ and Ar₂ were altered. After adding the amino group containing component stirring was conducted in case of pyrimidine derivatives for 2 hours and in case of triazine derivatives for 8–14 hours. The yields of the compounds of the general formula (I) obtained are contained in Table 6.

TABLE 6

| Number of Example | Ar₁ | Ar₂ | Catalyst | Additive | Temperature (°C.) | Time (hour) | Yield (%) |
|---|---|---|---|---|---|---|---|
| 48 | Phenyl- | 4-Methyl-6-methoxy-triazin-2-yl | PdCl₂ 145 mg | CH₃CN 0,2 cm³ | 25 | 6 | 70,8 |
| 49 | 4-Me-phenyl- | Phenyl- | Pd(Ph₃P)Cl₂ 70 mg | — | 60 | 3 | 87 |
| 50 | 4-Me-phenyl- | 2-Me-phenyl- | PdCl₂ 51 mg | CH₃CN 0,5 cm³ | 85 | 0,5 | 81 |
| 51 | 4-Me-phenyl- | 4-Methyl-6-methoxy-tri-azin-2-yl- | PdCl₂ 140 mg | CH₃CN 0,2 cm³ | 25 | 4,5 | 72 |
| 52 | 2-Cl-phenyl- | 2-Cl-phenyl- | PdCl₂ 70 mg | CH₃CN 1,0 cm³ | 25 | 14 | 86 |
| 53 | 2-Cl-phenyl- | 2-NO₂-phenyl- | PdCl₂ 68 mg | CH₃CN 2,0 cm³ | 25 | 3,5 | 95 |
| 54 | 2-Cl-phenyl- | 4-Pyridinyl- | PdCl₂ | CH₃CN | 25 | 6,5 | 72 |
| 55 | 2-Cl-phenyl- | 4,6-Dimethyl-pyrimidin-2-yl | PdCl₂ 60 mg | CH₃CN 2,0 cm³ | 65 | 0,75 | 93 |
| 56 | 2-Cl-phenyl- | 4-Methyl-pyrimidin-2-yl- | Pd(PhCN)₂Cl₂ 96 mg | PhCN 0,5 cm³ | 50 | 1,5 | 88 |
| 57 | 1-Thienyl- | Phenyl- | Pd(Ph₃P)₂Cl₂ 105 mg | — | 25 | 4 | 67 |
| 58 | 1-Naphthyl- | Phenyl- | Pd(Ph₃P)₂Cl₂ 97 mg | — | 50 | 2,5 | 72 |
| 59 | 4-Me-phenyl- | 4-Methyl-6-methoxy-ethoxy-tri-azin-2-yl | Pd(Ph₃P)₂Cl₂ 134 mg | — | 60 | 0,9 | 90 |
| 60 | 2-Cl-phenyl- | 4-Methyl-6-methoxy-tri-azin-2-yl | PdCl₂ 41 mg | CH₃CN 2,0 cm³ | 25 | 14 | 76 |

TABLE 6-continued

| Number of Example | Ar₁ | Ar₂ | Catalyst | Additive | Temperature (°C.) | Time (hour) | Yield (%) |
|---|---|---|---|---|---|---|---|
| 61 | 2-Br-phenyl- | 2-Cl-phenyl- | Pt(Ph₃P)₄ 21,5 mg Pd(Ph₃P)₂Cl₂ 66 mg | PhCN 0,5 cm³ | 70 | 2 | 77 |
| 62 | 2-Br-phenyl- | 4,6-Dimethyl-pyrimidin-2-yl- | PdCl₂ 67 mg | CH₃CN 0,3 cm³ | 80 | 1,1 | 85 |
| 63 | 2-Br-phenyl- | 4-Methyl-6-methoxy-triazin-2-yl | PdCl₂ 89 mg | CH₃CN 0,3 cm³ | 80 | 0,75 | 87 |

We claim:

1. A process for preparing a sulfonylurea of the formula $$Ar_1-SO_2-\underset{H}{N}-\underset{O}{\overset{\|}{C}}-\underset{H}{N}-Ar_2 \quad (I)$$

wherein
Ar₁ is a phenyl-, naphthyl- or thienyl moiety, or the derivatives thereof substituted by C₁₋₄ alkyl, C₁₋₄ haloalkyl, (halo)alkoxycarbonyl, (halo)alkyloxy, nitro, cyano moiety or by halogen atoms,
Ar₂ is a phenyl-, pyridyl-, pyrimidinyl or triazinyl moiety or the derivatives thereof substituted by C₁₋₄ (halo)alkyl, C₁₋₄ (halo)alkyloxy, amino, O-aryl-sulphonyl, O-(substituted carbamoyl)-moiety or by halogen atoms,
which comprises reacting
(a) an N-halogen-aryl-sulfonamidate of the formula $$Ar_1-SO_2-\underset{Y}{N}-X \quad (II)$$

wherein
Ar₂ has the above meaning,
X is chlorine or bromine, and
Y is sodium, potassium, quaternary ammonium or quaternary phosphonium moiety, with an aromatic amine of the formula $$Ar_2-NH_2 \quad (II)$$

wherein Ar₂ has the above meaning, in the presence of a carbonylation catalyst, and carbon monoxide; or
(b) reacting N-halogenoaryl-sulfonamidate of formula (II) with carbon monoxide in the presence of a carbonylation catalyst, and then reacting the mixture with an aromatic amine of formula (III); or
(c) reacting an N-halogenoarylamine of the formula $$Ar_2-\underset{Y'}{N}-X \quad (IV)$$

wherein
Ar₂ and X have the above meaning, and
Y' is hydrogen, sodium or potassium, with an arylsulfonamide of the formula $$Ar_1-SO_2-NH_2 \quad (V)$$

wherein Ar₁ has the above meaning, in the presence of a carbonylation catalyst and carbon monoxide; or
(d) reacting an amine of formula (III), with an amine N,N-dihalogenide of the formula $$Ar_2-NX_2 \quad (VI)$$

wherein Ar₂ and X₂ have the above meaning, with an arylsulfonamidate of formula (V) in the presence of a carbonylation catalyst and carbon monoxide, in a solvent at a temperature between from about −20° C. and about 130° C.

2. The process of claim 1, wherein in the sulonamidate of formula (II), X is chlorine, and Y is potassium.

3. The process of claim 1, wherein in the sulfonamidate of formula (II), X is chlorine, and Y is quaternary ammonium.

4. The process of claim 1, wherein the sodium or potassium salt of N-chloroaminotriazine is reacted with arylsulfonamide.

5. The process of claim 1, wherein the carbonylation is carried out a temperature between about 25°− and about 100° C.

6. The process of claim 1, wherein potassium-2-N-2-dichlorophenylsulfonamidate is reacted with 2-amino-4-methyl-6-methoxytriazine.

7. The process of claim 1, wherein 2-(N-chloroamino)-6-methyl-6-methoxytriazine sodium salt is reacted with 2-methoxy-carbonylbenzene-sulfonamide.

8. The process of claim 1, wherein the catalyst is palladium together with the carbonyls of the metals of group VI of the periodic table and/or with the complexes of the metals of group VIII of the periodic table.

9. The process of claim 1, further comprising a phase transfer catalyst added to the reaction.

10. The process of claim 9, wherein the phase transfer catalyst comprising from about 10⁻¹ to about 10% wt based on the N-halogen compound.

11. The process of claim 1, wherein the catalyst is a palladium containing complex formed by the coordinative bond between carbon, nitrogen, oxygen, phosphorous, sulfur, and/or halogen and is a homogeneous, heterogenous or immobilized homogeneous catalyst.

12. The process of claim 1, wherein the catalyst is present in an amount of from about 10⁻² to about 10% wt based on the N-halogen compound.

13. The process of claim 1 wherein the reaction is carried out in a solvent at a temperature between about −20° and about 130° C., under carbon monoxide with a partial pressure of from about 0.3 to about 10 mm/Hg within from about 0.5 to about 24 hours.

14. The process of claim 9, wherein the phase transfer catalyst is of the quaternary ammonium salt, quaternary phosphonium salt, or crown ether type.

15. A process for preparing a sulfonylurea of the formula $$Ar_1-SO_2-N-C-N-Ar_2 \quad (I)$$
$$\phantom{Ar_1-SO_2-N-}H\phantom{-}O\phantom{-}H$$

wherein
Ar$_1$ is phenyl, naphthyl- or thienyl moiety or the derivatives thereof substituted by $C_{1-4}$ alkyl, $C_{1-4}$ haloalkyl, (halo)alkoxycarbonyl, (halo)alkyloxy, nitro, cyano moiety, or by halogen atoms,
Ar$_2$ is a phenyl-, pyridyl-, pyrimidinyl or triazinyl moiety or the derivatives thereof substituted by $C_{1-4}$ (halo)alkyl, $C_{1-4}$ (halo)alkyloxy, amino, O-aryl-sulphonyl, O-(substituted carbamoyl)-moiety, or by halogen atoms, which comprises reacting a N-halogen-aryl-sulfonamidate of the formula $$Ar_1-SO_2-N-X \quad (II)$$
$$\phantom{Ar_1-SO_2-N-}Y$$

wherein
Ar$_1$ has the above meaning,
X is chlorine or bromine,
Y is a sodium, potassium, quaternary ammonium or quaternary phosphonium moiety, with an aromatic amine of the formula $$Ar_2-NH_2 \quad (II)$$

wherein Ar$_2$ has the above meaning, in the presence of a carbonylation catalyst and carbon monoxide.

16. The process of claim 15, further comprising a phase transfer catalyst.

* * * * *